United States Patent
Maruyama et al.

(10) Patent No.: US 8,514,388 B2
(45) Date of Patent: Aug. 20, 2013

(54) FLAW INSPECTING METHOD AND DEVICE THEREFOR

(75) Inventors: Shigenobu Maruyama, Oiso (JP);
Toshifumi Honda, Yokohama (JP);
Toshiyuki Nakao, Yokohama (JP); Yuta Urano, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/387,120

(22) PCT Filed: Jul. 28, 2010

(86) PCT No.: PCT/JP2010/004790
§ 371 (c)(1),
(2), (4) Date: Feb. 14, 2012

(87) PCT Pub. No.: WO2011/036838
PCT Pub. Date: Mar. 31, 2011

(65) Prior Publication Data
US 2012/0194807 A1 Aug. 2, 2012

(30) Foreign Application Priority Data
Sep. 24, 2009 (JP) ................... 2009-219264

(51) Int. Cl.
*G01N 21/95* (2006.01)
(52) U.S. Cl.
USPC ............ 356/237.2; 356/237.1; 356/237.4; 356/237.5
(58) Field of Classification Search
USPC ............... 356/237.1–237.5, 392–394
See application file for complete search history.

(56) References Cited

U.S. PATENT DOCUMENTS

| | | | |
|---|---|---|---|
| 4,708,484 A | 11/1987 | Komeyama et al. | |
| 5,712,701 A * | 1/1998 | Clementi et al. | 356/237.2 |
| 5,903,342 A * | 5/1999 | Yatsugake et al. | 356/237.4 |
| 6,104,481 A * | 8/2000 | Sekine et al. | 356/237.5 |
| 6,608,676 B1 | 8/2003 | Zhao et al. | |
| 6,778,267 B2 | 8/2004 | Drake | |
| 7,068,363 B2 * | 6/2006 | Bevis et al. | 356/237.5 |
| 7,528,942 B2 * | 5/2009 | Nakano et al. | 356/237.3 |
| 7,869,024 B2 * | 1/2011 | Urano et al. | 356/237.2 |
| 2003/0058432 A1 | 3/2003 | Drake | |
| 2008/0218751 A1* | 9/2008 | Togashi et al. | 356/237.5 |

(Continued)

FOREIGN PATENT DOCUMENTS

| | | |
|---|---|---|
| JP | 61-100930 | 5/1986 |
| JP | 5-209841 | 8/1993 |

(Continued)

*Primary Examiner* — Sang Nguyen
(74) *Attorney, Agent, or Firm* — Antonelli, Terry, Stout & Kraus, LLP.

(57) ABSTRACT

In order to maximize the effect of signal addition during inspection of foreign substances in wafers, a device structure including line sensors arranged in plural directions is effective. Low-angle detection optical systems that detect light beams in plural azimuth directions, the light beams being scattered in low angle directions among those scattered from a linear area on a sample illuminated by illuminating means, each include a combination of a first imaging lens group (330) and a diffraction grating (340) and a combination of a second imaging lens group (333) and an image detector (350) having a plurality of light receiving surfaces. A signal processing unit processes signals from the image detectors of the low-angle detection optical systems by adding the signals from the light receiving surfaces corresponding between the image detectors.

3 Claims, 12 Drawing Sheets

(56) References Cited

U.S. PATENT DOCUMENTS

| | | | |
|---|---|---|---|
| 2008/0304055 A1* | 12/2008 | Oshima et al. | 356/237.5 |
| 2009/0066940 A1 | 3/2009 | Matsui | |
| 2010/0118310 A1 | 5/2010 | Matsui | |
| 2010/0271625 A1 | 10/2010 | Matsui | |

FOREIGN PATENT DOCUMENTS

| | | |
|---|---|---|
| JP | 2008-58239 | 3/2008 |
| JP | 2008-268140 | 11/2008 |
| JP | 2008-309568 | 12/2008 |
| JP | 2009-68903 | 4/2009 |

* cited by examiner

LOW-ANGLE
DETECTION OPTICAL SYSTEM 121-1

LOW-ANGLE
DETECTION OPTICAL SYSTEM 121-2

LOW-ANGLE DETECTION OPTICAL SYSTEM 121-5

LOW-ANGLE DETECTION OPTICAL SYSTEM 121-6

FLAW INSPECTING METHOD AND DEVICE THEREFOR

TECHNICAL FIELD

The present invention relates to a flaw (or defect) inspection method and device for inspecting a micro-defect on a surface of a sample with high accuracy and at high speed.

BACKGROUND ART

In order to maintain or improve manufacturing yield of products manufactured in a manufacturing line for semiconductor devices, a foreign material that is attached onto a substrate (wafer), a flaw that occurs on a surface of the substrate, defective crystal or the like is inspected during a process of manufacturing the semiconductor devices. For example, in order to manage dust in an etching device or a sputtering device, a dummy wafer that has a surface whose cleanness degree (the number of foreign materials, a distribution of the foreign materials on the surface, or the like) is known is placed in a process device, transported within the process device, and carried out of the process device after a dummy operation. Then, the surface of the wafer is inspected. The cleanness degree of the wafer surface is compared before and after the process. If it turns out that the number of foreign materials is increased with the process by the device, the operation of the device is stopped for cleaning and maintenance.

In a conventional semiconductor manufacturing process, the presence of a foreign material having several tens of nanometers in diameter could cause a reduction in the yield of manufacturing the semiconductors. In order to maintain high yield of manufacturing semiconductor substrates, it is significant to swiftly detect abnormality (occurrence of dust in a manufacturing device) in the manufacturing device and suppress defective products at work. In addition, for a device for inspecting a wafer surface, improving sensitivity (or detect a minute foreign material) of the device is highly demanded.

An example of the inspection device for such a purpose is disclosed in Patent Document 1. Patent Document 1 discloses a device configured to irradiate, with laser light, a surface of a rotating and translating wafer and detect scattered laser light scattered from a foreign material attached to the wafer surface. Patent Document 1 further discloses a method for processing a detected signal for the purpose of a high sensitivity. In the conventional example of Patent Document 1, a plurality of optical systems for detecting scattered light are arranged (in a plurality of azimuth directions and a plurality of elevation directions) around a point on the wafer that is to be irradiated with the laser light. The high sensitivity is achieved by applying directivity of a light component (background noise component) scattered due to roughness of the wafer surface to weighted adding process of a plurality of detected signals.

In addition, Patent Document 2 discloses a device configured to irradiate, with laser light, a surface of a rotating and translating wafer and detect light generated and scattered from a foreign material attached to the surface of the wafer. Patent Document 2 further discloses a method for causing a line sensor to detect light from regions formed by dividing a region irradiated with the laser light in the configuration of the device. In the conventional example of Patent Document 2, a plurality of optical systems for detecting scattered light are arranged (in a plurality of azimuth directions and a plurality of elevation directions) around a point on the wafer and is to be irradiated with the laser light. However, the line sensor that has multiple pixels is used as a light receiver. A light receiving surface of the line sensor is in a conjugate relationship with the position of the point on the wafer and is irradiated with the laser light. Thus, the position of the point on the wafer and is irradiated with the laser light is imaged and observed. A light component (background noise component) scattered due to roughness of the surface of the wafer is assigned to each of the pixels of the line sensor and detected. Thus, background noise that is detected for each of the pixels of the line sensor is reduced.

In addition, a high sensitivity is achieved by repeatedly detecting the same defect (foreign material) multiple times and summing detected signal components.

In addition, Patent Document 3 discloses an inspection device configured to irradiate a surface of a rotating wafer from an oblique direction with light linearly formed by a cylindrical lens, and with a CCD, detect light scattered in a direction perpendicular to a direction of extension of a linear region (irradiated with the light and laying on the surface of the wafer) or a direction oblique to the surface of the wafer and thereby detects a defect.

In addition, Patent Document 4 discloses the configuration of an optical system for observing, from an oblique direction, a surface of an object to be inspected.

In a conventional example described in Patent Document 4, a relay lens is located at an elevation of 30 degrees with respect to the surface of the object to be inspected, and an intermediate image of the surface of the object to be inspected is formed on a diffraction grating. The intermediate image is magnified by an objective lens that faces the diffraction grating, then, the intermediate image is observed by an image sensor. With the configuration, even when the surface of the sample is observed from an oblique direction at a different azimuth, fields of all observation optical systems can match each other. By optimizing a periodic structure (the number of grooves and blaze angles) of the diffraction grating, light that is incident on the diffraction grating is diffracted as first-order diffracted light in the normal direction of the diffraction grating and efficiently incident on the objective lens.

CITATION LIST

Patent Literature

Patent Literature 1: JP-A-2008-58239
Patent Literature 2: JP-A-2008-268140
Patent Literature 3: U.S. Pat. No. 6,608,676
Patent Literature 4: U.S. Pat. No. 6,778,267

SUMMARY OF INVENTION

Technical Problems

In the inspection method disclosed in Patent Document 1, the sensitivity for detecting a defect is significantly affected by dimensions of a region to be irradiated with the laser light. Specifically, as the region to be irradiated with the laser light is larger, the ratio of a light component (background noise component) scattered due to roughness of the wafer surface to a light component (signal component) generated from a foreign material attached to the wafer is larger. Therefor, the sensitivity for detecting a defect is reduced. In order to improve the sensitivity for detecting a defect, it is effective to reduce the area of the region to be irradiated with the laser light and thereby increase the ratio of the signal component to the background noise component. However, if the area of the region to be irradiated with the laser light is reduced, a time necessary to inspect the entire wafer surface is increased. Thus, in the conventional example of Patent Document 1, it is difficult to improve the sensitivity for detecting a defect while maintaining a throughput for the inspection.

In the configuration described in Patent Document 2, a region that lies on the wafer and is irradiated with the laser light is divided into the regions, and the divided regions are detected by the plurality of pixels (line sensor). The sensitivity for detecting a defect is not affected by the area of the region to be irradiated with the laser light. The detection method is suitable for the purpose of achieving the high sensitivity while maintaining a throughput for inspection. However, in the configuration of the detection optical systems disclosed in Patent Document 2, not all fields of the plurality of detection optical systems (6 detection optical systems) arranged at different azimuths can match on the wafer. Accordingly, it is not possible to simultaneously detect laser light (generated and scattered from the same defect) from all azimuth directions. Therefor, it is not possible to obtain an effect of improving the sensitivity for detecting a defect by summing signals detected from the six azimuth directions.

In addition, in the configuration of the device described in Patent Document 3, only light that is scattered in a direction perpendicular to the direction of extension of a linear region that lies on the wafer and is irradiated is detected. Patent Document 3 does not describe that a variety of scattered light such as forward-scattered light, backward-scattered light and upwardly scattered light are to be detected.

In addition, in the configuration described in Patent Document 4, when light that is detected from the surface of the sample has a polarization characteristic, the diffraction efficiency (light use efficiency) of the diffraction grating varies in characteristic depending on the polarization of the detected light. As a result, there is a problem that the light use efficiency of the entire detection optical system varies.

In general, the diffraction efficiency of a diffraction grating varies depending on a polarization direction (direction in which an electric field vector vibrates) of incident light. When the surface of the sample is irradiated with polarized light, or when light that is reflected or scattered from the surface of the sample has a polarization characteristic due to a foreign material or defect that lies on the wafer surface, the brightness of an image to be observed may be changed or sufficient amount of light for the observation may not be obtained. In such cases, the effect of improving the sensitivity for detecting a defect cannot be obtained. In addition, in the conventional example of Patent Document 4, since the observation magnification of the relay lens is 1, a detection elevation that is defined using the sample surface as a reference and at which light is detected is equal to an incidence elevation that is defined by the surface of the diffraction grating and a direction in which light (main optical axis) is incident on the surface of the diffraction grating.

When the detection elevation at which the light that is reflected or scattered from the surface of the sample is detected is reduced, the incidence elevation at which the light is incident on the surface of the diffraction grating is also reduced. When the incidence elevation at which the light is incident on the surface of the diffraction grating is reduced, there is a problem that the diffraction efficiency is reduced.

An object of the present invention is to provide a method and device for inspecting a surface, which allows for improvement in defect detection sensitivity without reducing throughput for inspection.

Solution to Problem

In order to accomplish the aforementioned object, according to the present invention, a device for inspecting a defect includes: table means for holding a sample thereon; illumination means for illuminating a linear region that lies on the sample held by the table means; high-angle detection optical system means for detecting, from plural azimuth directions, light scattered from the linear region that lies on the sample illuminated by the illumination means, the scattered light being scattered from the linear region at a high evaluation; plural low-angle detection optical system means having plural optical image detectors, the optical image detectors detecting, from plural azimuth directions, light that is among the light scattered from the linear region illuminated by the illumination means and laying on the sample and has been scattered from the linear region at a low evaluation, the low-angle detection optical system having an optical image detector; and a signal processing unit that processes a signal obtained by detecting the light scattered from the sample by means of the high-angle detection optical system means and a signal obtained by detecting the light scattered from the sample by means of the low-angle detection optical system means to detect a defect on the sample, wherein the optical image detector of the low-angle detection optical system means is formed by synthesizing a first imaging lens group, a diffraction grating, a second imaging lens group and an image detector having plural light receiving surfaces, and wherein the signal processing unit sums and processes signals detected by light receiving surfaces that are included in the plural optical image detectors of the low-angle detection optical system means and correspond to each other.

In addition, in order to accomplish the aforementioned object, according to the present invention, a device for inspecting a defect includes: table means capable of holding a sample, rotating the sample and moving the sample in a certain direction; illumination means for illuminating, from an oblique direction or a vertical direction, a linear region that lies on the sample held by the table means; imaging means that has plural imaging optical systems for receiving, from at least four azimuth directions, light scattered in a first elevation direction from the linear region that lies on the sample illuminated by the illumination means, imaging the linear region, and acquiring plural images of the linear region laying on the sample; and a signal processing unit that synthesizes and processes the plural images acquired by imaging the linear region by means of the plural imaging optical systems of the imaging means and thereby detects a defect on the sample.

In addition, in order to accomplish the aforementioned object, according to the present invention, a method for inspecting a defect includes the steps of: illuminating, from an oblique direction, a linear region that lies on a sample; receiving, from at least four azimuth directions, light scattered from the illuminated linear region laying on the sample, imaging the linear region, and acquiring plural images of the linear region laying on the sample; synthesizing the plurality of the acquired images to form a synthesized image; and processing the synthesized image and thereby detecting a defect that lies on the sample.

Advantageous Effects of Invention

According to the present invention, it is possible to provide a defect inspection method and device, which inhibit a pixel from being shifted due to a variation in the height of a wafer or can suppress an influence of shifting of a pixel even when imaging optical systems are arranged in plural directions, and which enables for signals of light scattered from substantially the same region to be summed and a detection sensitivity to be improved.

DESCRIPTION OF EMBODIMENTS

Figure 1:
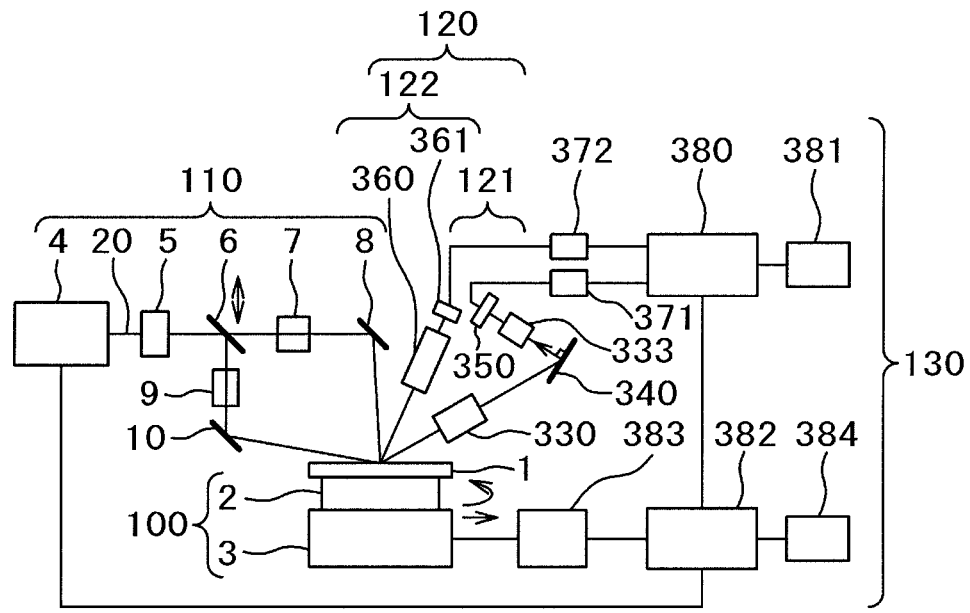
FIG. 1 is a block diagram illustrating an outline configuration of a defect inspection device according to a first embodiment.

Embodiments of the present invention are described with reference to the accompanying drawings.

First Embodiment

The configuration of a surface inspection device according to a first embodiment of the present invention is described with reference to FIG. 1.

The surface inspection device includes a stage unit 100, an illumination optical system 110, a detection optical system 120 and a processing control unit 130.

The stage unit 100 includes a rotary table 2 and a stage 3. The rotary table 2 is capable of rotating while holding a substrate (wafer) 1 to be inspected thereon. The stage 3 is capable of moving at least one direction in a plane.

The illumination optical system 110 includes a laser light source 4, a beam optical system 5, an optical path changing mirror 6, a (first) laser forming unit 7, a mirror 8, a (second) laser forming unit 9 and a mirror 10. The laser light source 4 emits a laser 20 that has a wavelength in the ultraviolet (UV) range or the deep ultraviolet (DUV) range. The beam optical system 5 increases the diameter of the laser 20 emitted by the laser light source 4 and forms the laser 20. The optical path changing mirror 6 is located on an optical path of the laser 20 output from the beam optical system 5. The optical path changing mirror 6 is inserted into and retracted from the optical path of the laser 20 by a driving mechanism (not illustrated) and changes the optical path of the laser 20. The (first) laser forming unit 7 forms the laser 20 that has passed straight through the optical path changing mirror 6 while the optical changing mirror 6 is retracted from the optical path of the laser 20. The mirror 8 reflects the laser 20 that has passed through the (first) laser forming unit 7 so that a linear region 21 on the wafer 1 is illuminated with the laser 20 from a direction that is substantially perpendicular to the surface of the wafer 1. The (second) laser forming unit 9 forms the laser 20 reflected by the optical path changing mirror 6 while the optical path changing mirror 6 is inserted into the optical path of the laser 20. The mirror 10 reflects the laser 20 that has passed through the (second) laser forming unit 9 so that the laser 20 is incident on the wafer 1 from a direction oblique to the surface of the wafer 1 and the linear region 21 is illuminated with the laser 20 from the oblique direction.

The detection optical system 120 includes low-angle detection optical systems 121 and high-angle detection optical systems 122. The low-angle detection optical systems 121 each detect light reflected and scattered at a relatively low angle from the substrate 1 having the linear region 21 illuminated by the illumination optical system 110. The high-angle detection optical systems 122 each detect light reflected and scattered at a relatively high angle from the substrate 1 having the linear region 21 illuminated by the illumination optical system 110.

The low-angle detection optical systems 121 each include a first imaging optical system 330, a diffraction grating 340, a second imaging optical system 333, an optical detector 350 and an A/D converter 371. The first imaging optical system 330 collects light reflected and scattered from the substrate 1 at a relatively low angle and forms an image. The diffraction grating 340 is located at a position where the first imaging optical system 330 forms the image. The second imaging optical system 333 forms an image of light diffracted by the diffraction grating 340. The optical detector 350 detects the optical image formed by the second imaging optical system 333. The A/D converter 371 converts an analog signal output from the optical detector 350 into a digital signal.

The high-angle detection optical systems 122 each include an optical system 360, an optical detector 361 and an A/D converter 372. The optical system 360 collects light reflected and scattered from the substrate 1 at a relatively high angle. The optical detector 361 detects the light reflected and scattered from the wafer 1 and collected by the optical system 360. The A/D converter 372 converts an analog signal output from the optical detector 361 into a digital signal.

Figure 2:
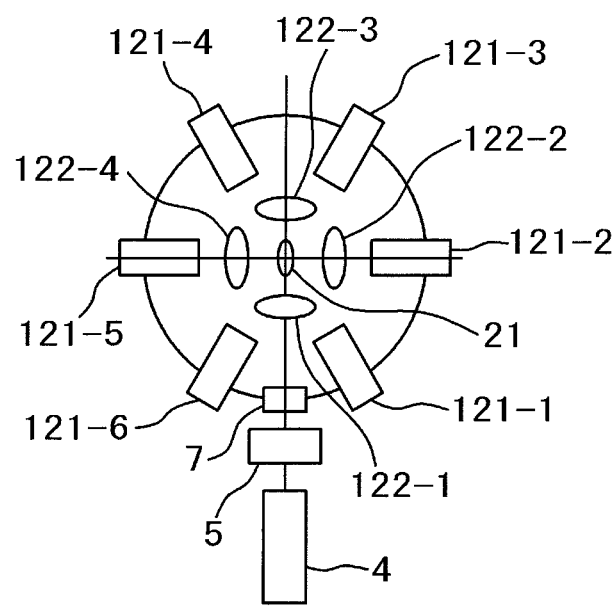
FIG. 2 is a plan view illustrating an arrangement of an illumination optical system, a high-angle detection optical system and a low-angle detection optical system, which are included in the defect inspection device according to the first embodiment.

The low-angle detection optical systems 121 and the high-angle detection optical systems 122 are units that are arranged around the linear region 21 that is illuminated by the illumination optical system 110 on the wafer 1 as illustrated in FIG. 2. Specifically, the low-angle detection optical systems 121 are units 121-1 to 121-6 that are arranged around the linear region 21 on the substrate 1, while the high-angle detection optical systems 122 are units 122-1 to 122-4 that are arranged around the linear region 21 on the substrate 1.

The processing control unit 130 includes a signal processing unit 380, a stage controller 383 and a controller 382. The signal processing unit 380 processes detected signals (output from the detection optical system 120) of light scattered from the wafer 1. The stage controller 383 receives a result of the processing performed by the signal processing unit 380 and controls the stage unit 100. The controller 382 controls the light source 110, the detection optical system 120 and the signal processing unit 380.

Next, a detailed configuration of each of the low-angle detection optical systems 121 is described.

The low-angle detection optical systems 121 and the high-angle detection optical systems 122 are arranged as illustrated in FIG. 2, and the linear region 21 on the wafer 1 is illuminated with the laser 20. When the imaging is performed from a direction (direction in which the units 121-2 and 121-5 are arranged) perpendicular to the direction in which the linear region 21 of the wafer 1 extends, an optical image can be formed on a surface of a sensor by focusing on the linear region 21 on the wafer 1 with a combination of a general collecting lens and a general imaging lens and the optical image can be detected. However, when the imaging is performed from directions (directions in which the units 121-1, 121-3, 121-4 and 121-6 are arranged) which are not perpendicular to the direction in which the linear region 21 of the wafer 1 extends, focusing on the range to be imaged in the linear region 21 on the wafer 1 is difficult to perform. Therefore, imaging a focused optical image and detecting thereof become difficult to perform.

The optically systems employed in the present embodiment are capable of focusing the whole range to be imaged in the linear region 21 on the wafer 1, illuminated with the laser 20, so as to image the linear region 21 on the wafer 1 from any direction.

Figure 3:
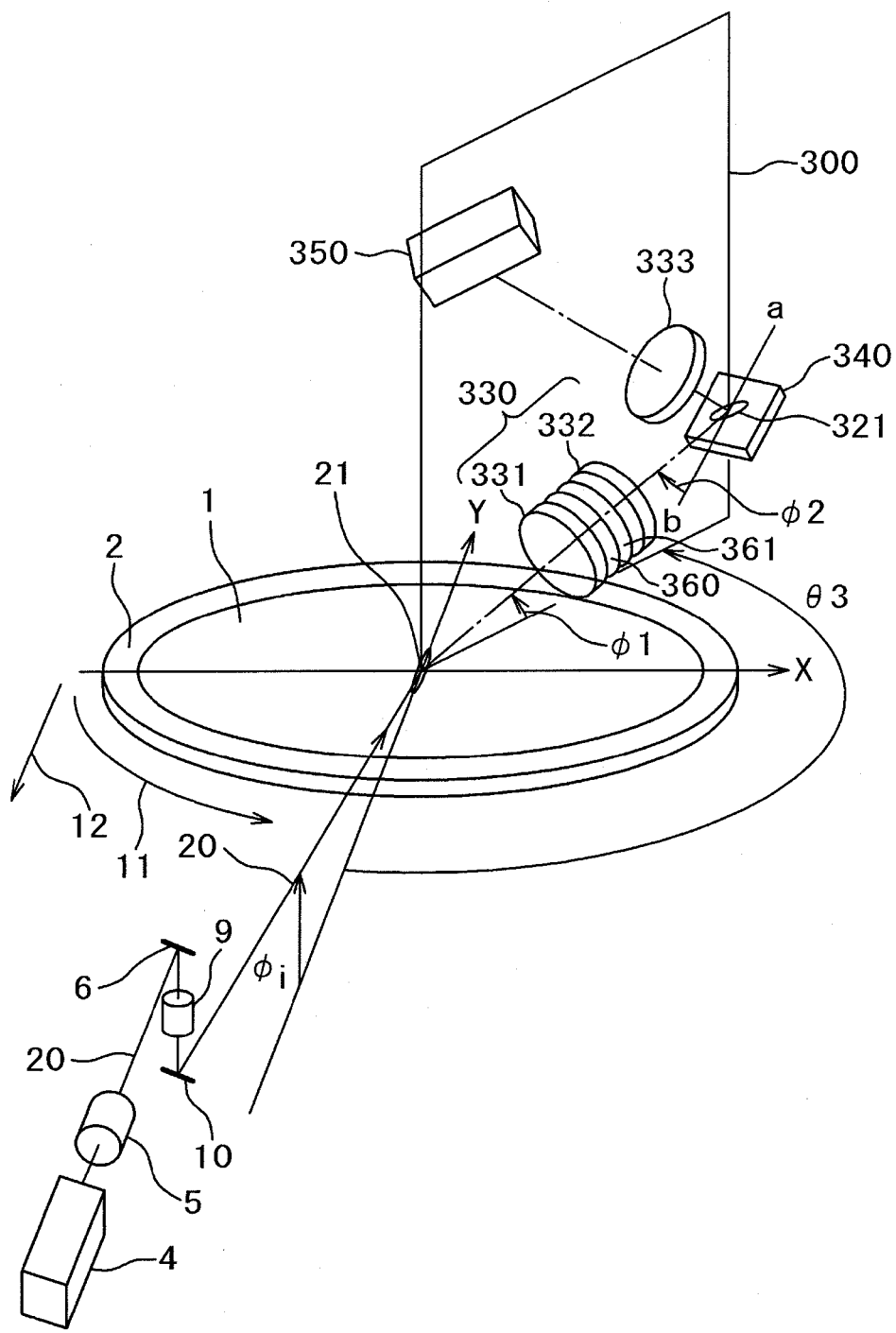
FIG. 3 is a perspective view illustrating positional relationships among an oblique illumination optical system, a wafer and the low-angle detection optical system.

FIG. 3 is a perspective view illustrating a basic configuration of the low-angle detection optical system 121 according to the present invention. FIG. 3 illustrates relationships among the low-angle detection optical system 121-1 illustrated in FIG. 2 (illustrating the planar arrangement of the detection optical system 120), the laser light source 4 of the illumination optical system 110 and the beam optical system 5 of the illumination optical system 110. In addition, FIG. 3 illustrates the state in which the laser 20 emitted by the laser light source 4 is reflected by the optical path changing mirror 6 and further reflected by the mirror 10 in the illumination optical system 110. The laser is incident on the wafer 1 from a direction oblique to the surface of the wafer 1 so that the linear region 21 is illuminated from the oblique direction in the configuration illustrated in FIG. 1.

The linear region 21 on the wafer 1 is illuminated with the laser 20 emitted by the laser light source 4 from an incidence angle direction with an elevation $\phi i$ with the surface of the wafer 1, the wafer 1 is vacuumed by means (not illustrated) onto the rotary stage 2 of the stage unit 100. In the present embodiment, a third harmonic (with a wavelength of 355 nm) of a YAG laser that is emitted from a laser oscillator included in the laser light source 4 is used as the laser 20. After the aforementioned laser light source 4 emitted the laser 20, the beam forming optical system 5 increases the diameter of the laser 20, forming the laser 20. The linear region 21 on the surface of the wafer 1 is irradiated with the laser 20 in a direction parallel to the Y axis. The linear region 21 on the surface of the wafer 1 is irradiated with the laser 20 has a dimension of 30 μm (in the X-axis direction) and a dimension of 400 μm (in the Y-axis direction). The angle (elevation) $\phi i$ of the incidence of the laser 20 on the surface of the wafer 1 is 20 degrees.

The rotary table 2 rotates at a certain angular velocity in a direction indicated by an arrow 11 and the stage 3 translates along the Y-axis direction (direction indicated by an arrow 12) at the same time. Accordingly, the linear region 21 on the surface of the wafer 1 illuminated with the laser 20 spirally moves on the surface of the wafer 1 thereby the entire surface of the wafer 1 is scanned.

Figure 4:
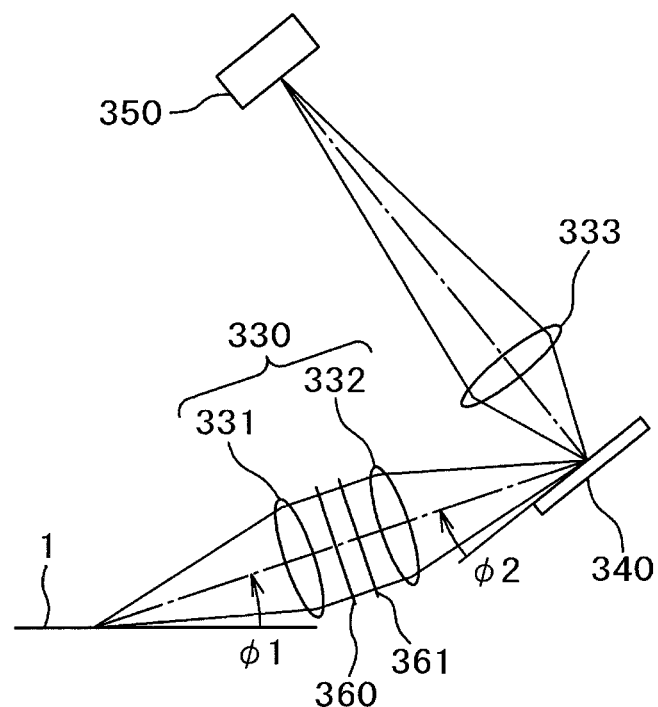
FIG. 4 is a side view illustrating an outline configuration of an oblique detection optical system.

Among light scattered from the linear region 21 that is illuminated with the laser 20 on the surface of the wafer 1, light that is scattered at an azimuth $\theta 3$ is detected by the low-angle detection optical system 121-1 located at the azimuth θ3. The azimuth θ3 is defined by using an incidence azimuth as a standard. Reference numeral 330 indicates the first imaging optical system which includes an objective lens 331 and an imaging lens 332. Reference numeral 360 indicates an analyzer (polarization filter) and reference numeral 361 indicates a half-wavelength plate, the analyzer allows transmitting only a scattered light component polarized in a specific direction. Next, the configuration of the low-angle detection optical system 121-3 is described referring to FIG. 4. FIG. 4 illustrates an optical path of the low-angle detection optical system 121-3, while the optical path of the low-angle detection optical system 121-3 is located on a plane 300 (plane that is perpendicular to the surface of the wafer 1 and the azimuth of the plane is θ3) illustrated in FIG. 3. A numerical aperture (NA) of the objective lens 331 is 0.3. A detection field of the objective lens 331 is a diameter of 0.5 mm and covers the linear region 21 on the wafer 1. An intermediate image 321 of light that is reflected and scattered from the linear region 21 irradiated with the laser 20 is formed on the diffraction grating 340 through the imaging lens 332. In this case, an imaging magnification m1 is 1.

A correlation among the imaging magnification m1 of the first imaging optical system 330, the detection elevation φ1 at which light that comes from the linear region 21 is incident on the objective lens 331 and the incidence elevation φ2 defined by the incidence of a main optical axis on the diffraction grating 340 is expressed by $$\tan \phi 1/\tan \phi 2 = m1 \quad \text{(Equation 1)}$$

As expressed by Equation 1, when the imaging magnification m1 of the first imaging optical system 330 is 1, the angles φ1 and φ2 are equal to each other. In the present embodiment, the angles φ1 and φ2 are both 30 degrees.

In addition, an angular magnification (ratio of a numerical aperture on the side of an image to a numerical aperture on the side of the object) of the first imaging optical system 330 and the imaging magnification m1 represent the same correlation as expressed by Equation 1. The light is incident on the diffraction grating 340 with the numerical aperture of the imaging lens 332 is 0.3 which is the same numerical aperture of the objective lens 331.

When the surface of the wafer 1 is magnified and observed by the imaging optical system 330, the elevation p2 defined by the incidence of a main optical axis on the diffraction grating 340 tends to be small. For example, when φ1=30° and the imaging magnification m1 is 2, φ2=16.1°. The diffraction grating 340 is a blazed diffraction grating in which a minute periodic groove pattern is formed on the surface thereof. The diffraction grating 340 is designed to maximize a diffraction efficiency of incident and positive first-order diffracted light. The structure of the diffraction grating 340 is described later.

The intermediate image 321 that is formed on the diffraction grating 340 by the first imaging optical system 330 is magnified by the second imaging optical system 333 that is arranged in the normal direction of the diffraction grating 340. Then, the intermediate image 321 is formed on a light receiving surface of the optical detector 350. An imaging magnification of the second imaging optical system 333 is indicated by m2.

Figure 5:
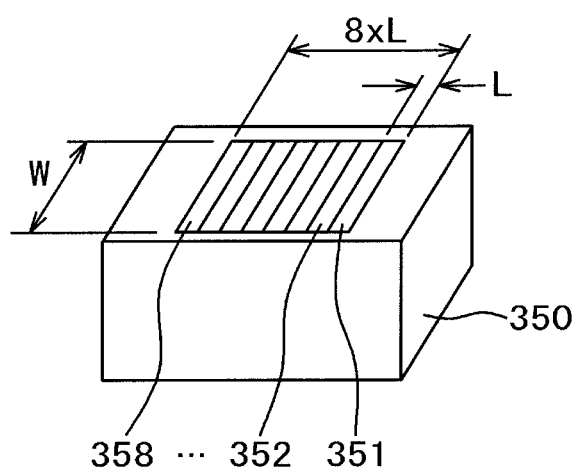
FIG. 5 is a perspective view of a line sensor.

FIG. 5 illustrates an outline configuration of the optical detector 350. The optical detector 350 is a photomultiplier (of a multi-anode type) having a plurality of light receiving surfaces. In the present embodiment, the optical detector 350 is structured with 8 channels (351 to 358) of pixels are arrayed, wherein each pixels is 7 mm in width W and 1.5 mm in length L. Signals of the 8 channels are detected in parallel by a signal detection circuit described in later and can be independently used for signal processing.

Figure 6A:
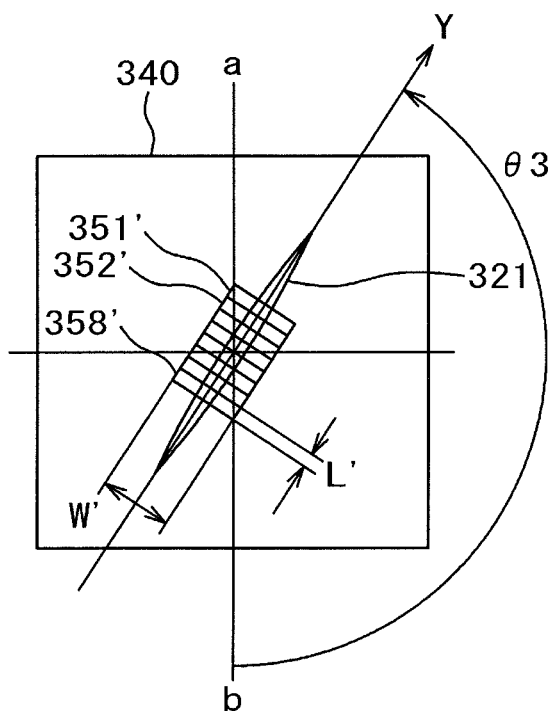
FIG. 6A is a plan view illustrating positional relationships among a diffraction grating, a light receiving element of the line sensor viewed from the side of the diffraction grating, and an image that is projected on the diffraction grating and represents an illuminated linear region that lies on the wafer.
Figure 6B:
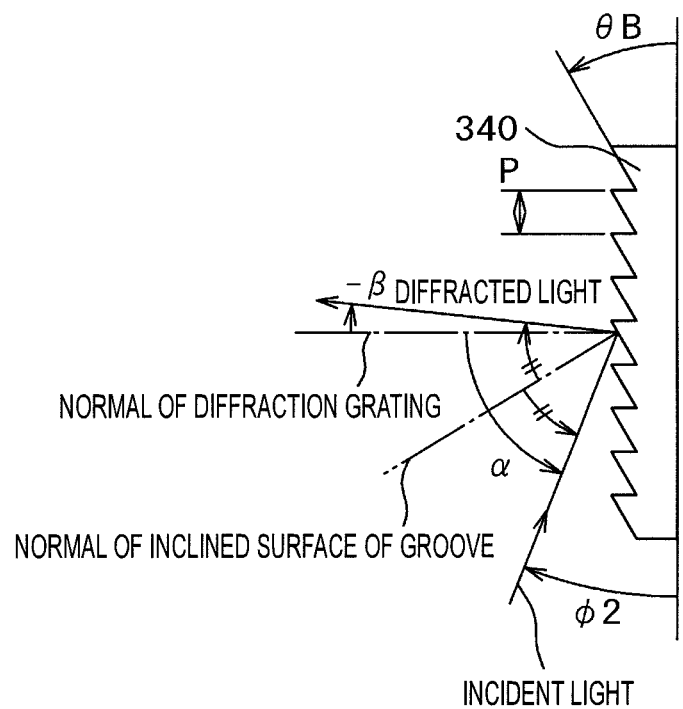
FIG. 6B is a side cross-sectional view of the diffraction grating.

FIGS. 6A and 6B illustrate relationships between the light receiving surfaces (351 to 358) of the optical detector 350 and the intermediate image 321 that is formed on the diffraction grating 340 and represents the linear region 21 on the surface of the wafer 1 illuminated with the laser 20. As illustrated in FIG. 6A, Y axis (a longitudinal direction of the intermediate image 321) on the surface of the wafer forms, on the diffraction grating 340, an angle θ3 with an axis a-b within the surface of the diffraction grating 340.

This angle θ3 is equal to the azimuth θ3 at which the low-angle detection optical system 121-1 detects the light. The axis a-b is a line that crosses the surface of the diffraction grating 340 and the plane 300. The optical detector 350 is rotated so that the array direction of the light receiving surfaces (351' to 358') of the optical detector 350 are arranged in parallel to Y axis. In this case, the optical detector 350 is rotated within a plane that is perpendicular to the normal of the diffraction grating 340.

FIG. 6A illustrates the state in which the imaging magnification m2 of the second imaging optical system 333 is 50.

Specifically, when the surface of the diffraction grating 340 is used as a reference, the light receiving surfaces (351 to 358) of the optical detector 350 are imaged on the diffraction grating 340 so that the images of the light receiving surfaces (351 to 358) of the optical detector 350 are reduced to one fiftieth (351' to 358') of the original. Accordingly, the dimension of each light receiving surface (351 to 358) is 140 μm in width (W') and 30 μm in length (L'). The dimension of the intermediate image 321 of the linear region 21 is 30 μm (in the X-axis direction) and 400 μm (in the Y-axis direction).

As described above, the minute periodic groove pattern is formed on the surface of the diffraction grating 340. The minute periodic groove pattern is formed in a sawtooth shape. FIG. 6B schematically illustrates diffracted light when the light is incident on the surface of the diffraction grating 340 at an incident angle α (corresponding to an angle of (90°−φ2)). In a blazed diffraction grating, when a diffraction efficiency of a specific order of diffraction is to be maximized, it is necessary to satisfy correlations (expressed by Equations 2 and 3) among an output angle β, a diffraction order m, and a wavelength λ of the illumination light.

$$\sin \alpha + \sin \beta = Nm\lambda \quad \text{(Equation 2)}$$

In Equation 2, N is the number of grooves per millimeter. In the present embodiment, the incidence elevation φ2 is 30 degrees. The number N of grooves per millimeter is 2440 (pitches between the grooves P are 0.41 μm) when the angle α is 60 degrees, the angle β is set to 0 degrees in order to cause the diffracted light to be output from the diffraction grating 340 in the direction of the normal of the diffraction grating 340, the diffraction order m is 1 in order to use positive first-order diffracted light, and the wavelength λ of the illumination light is 355×10⁻³ mm.

$$\theta B = (\alpha + \beta)/2 \quad \text{(Equation 3)}$$

In Equation 3, θB is an angle of an inclined surface of each of grooves formed on the surface of the diffraction grating 340.

In the present embodiment, when setting α=60 degrees and β=0 degrees, then calculated as θB=30 degrees. A structure of the diffracting grating, which maximizes the diffraction efficiency of the first-order diffracted light, can be designed based on Equations 2 and 3. As described with reference to FIG. 4, the light is incident on the diffraction grating 340 with the numerical aperture on the side of the incident light on the diffraction grating 340 is 0.3 and equal to the numerical aperture of the objective lens 331 on the side of the incident light on the objective lens 331. Thus, the diffracted light from the surface of the diffraction grating 340 spreads in the same range as the spreading range of the incident light on the diffracting grating 340. It is necessary that the numerical aperture of the incidence side of the second imaging optical system 333 be equal to or larger than the numerical aperture of the incidence side of the diffraction grating 340. In the present embodiment, the second imaging optical system 333 is configured so that the numerical aperture of the second imaging optical system 333 on the side of the incident light on the second imaging optical system 333 is 0.4.

FIGS. 7A to 7F illustrate relationships between the pixels of the optical detectors and intermediate images that are formed on the diffraction gratings of the low-angle detection optical systems 121-1 to 121-6 and represent the linear region 21 illuminated with the laser 20 on the surface of the wafer 1.

Figure 7A:
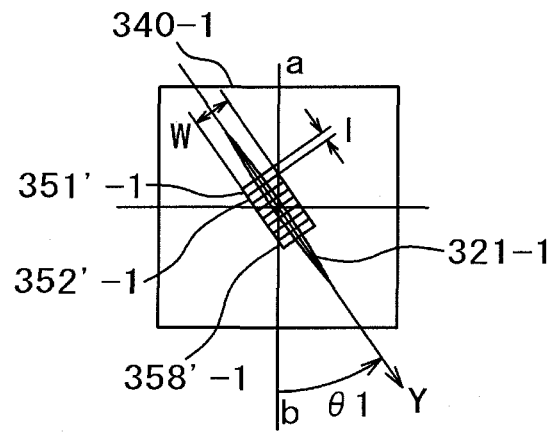
FIG. 7A is a plan view of a diffraction grating and illustrates positional relationships among a diffraction grating, a light receiving element of the line sensor viewed from the side of the diffraction grating, and an image that is projected on the diffraction grating and represents an illuminated linear region that lies on the wafer in a low-angle detection optical system and arranged in a direction deviated by an angle of θ1 with respect to the angle of incidence.

FIG. 7A is a diagram illustrating the relationship between pixels (351'-1 to 358'-1) of an optical detector 350-1 and an intermediate image 321-1 that is formed on a diffraction grating 340-1 of the low-angle detection optical system 121-1 (illustrated in FIG. 2) and represents the linear region 21 illuminated with the laser 20 on the surface of the wafer 1. The axis a-b matches an azimuth direction in which the low-angle detection optical system 121-1 detects light. Y axis (the longitudinal direction of the linear region 21 that is illuminated with the laser 20 and lies on the surface of the wafer 1, or a longitudinal direction of the intermediate image 321-1 of the laser 20) on the surface of the wafer 1 forms an angle θ1 with the axis a-b.

Figure 7B:
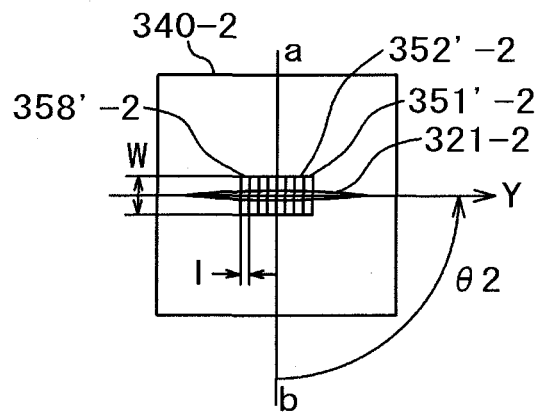
FIG. 7B is a plan view of a diffraction grating and illustrates positional relationships among a diffraction grating, a light receiving element of the line sensor viewed from the side of the diffraction grating, and an image that is projected on the diffraction grating and represents an illuminated linear region that lies on the wafer in a low-angle detection optical system and arranged in a direction deviated by an angle of θ2 with respect to the angle of incidence.
Figure 7C:
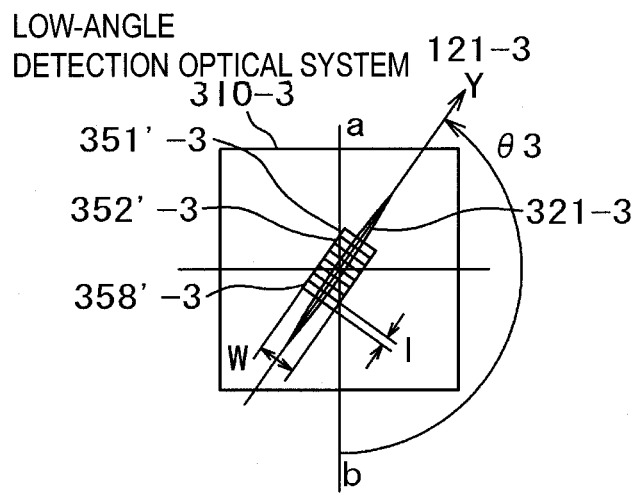
FIG. 7C is a plan view of a diffraction grating and illustrates positional relationships among a diffraction grating, a light receiving element of the line sensor viewed from the side of the diffraction grating, and an image that is projected on the diffraction grating and represents an illuminated linear region that lies on the wafer in a low-angle detection optical system and arranged in a direction deviated by an angle of θ3 with respect to the angle of incidence.
Figure 7D:
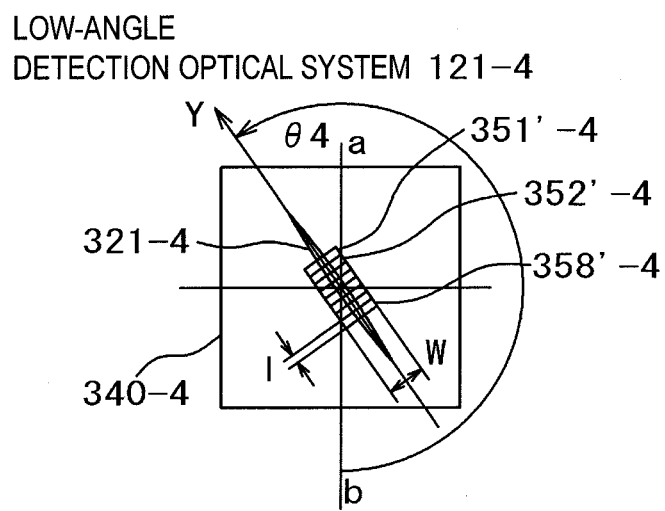
FIG. 7D is a plan view of a diffraction grating and illustrates positional relationships among a diffraction grating, a light receiving element of the line sensor viewed from the side of the diffraction grating, and an image that is projected on the diffraction grating and represents an illuminated linear region that lies on the wafer in a low-angle detection optical system and arranged in a direction deviated by an angle of θ4 with respect to the angle of incidence.
Figure 7E:
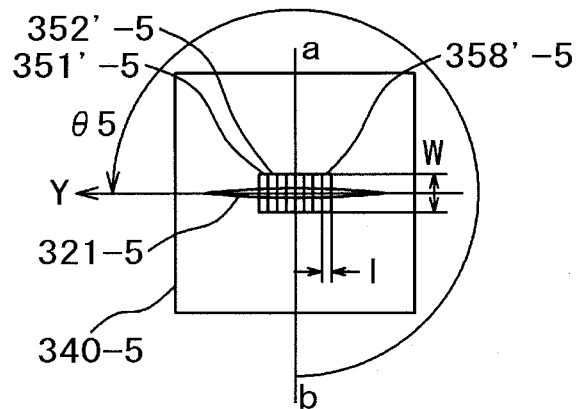
FIG. 7E is a plan view of a diffraction grating and illustrates positional relationships among a diffraction grating, a light receiving element of the line sensor viewed from the side of the diffraction grating, and an image that is projected on the diffraction grating and represents an illuminated linear region that lies on the wafer in a low-angle detection optical system and arranged in a direction deviated by an angle of θ5 with respect to the angle of incidence.
Figure 7F:
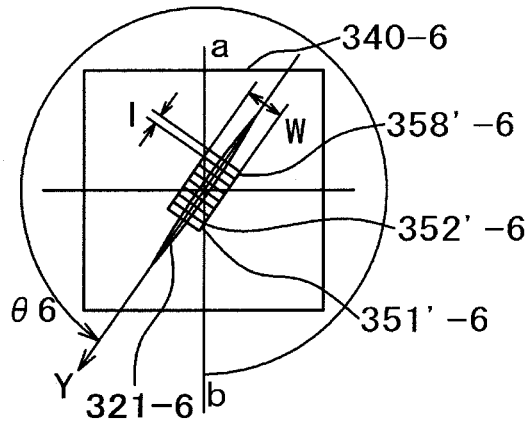
FIG. 7F is a plan view of a diffraction grating and illustrates positional relationships among a diffraction grating, a light receiving element of the line sensor viewed from the side of the diffraction grating, and an image that is projected on the diffraction grating and represents an illuminated linear region that lies on the wafer in a low-angle detection optical system and arranged in a direction deviated by an angle of θ6 with respect to the angle of incidence.

FIG. 7B is a diagram illustrating the relationship between the pixels (351'-1 to 358'-1) of the optical detector 350-2 and an intermediate image 321-2 that is formed on a diffraction grating 340-2 of the low-angle detection optical system 121-2 (illustrated in FIG. 2) and represents the linear region 21 illuminated with the laser 20 on the surface of the wafer 1. The axis a-b matches an azimuth direction in which the low-angle detection optical system 121-2 detects light. Y axis (the longitudinal direction of the linear region 21 that is illuminated with the laser 20 and lies on the surface of the wafer 1, or a longitudinal direction of the intermediate images 321-2 of the laser 20) on the surface of the wafer 1 forms an angle θ2 with the axis a-b.

Similarly as above, FIGS. 7C to 7F illustrate the relationships between the pixels (351'-1 to 358'-1) of the optical detectors 350-3 to 350-6 and intermediate images 321-3 to 321-6 that are formed on diffraction gratings 340-3 to 340-6 of the low-angle detection optical systems 121-3 to 121-6 (illustrated in FIG. 2) and represent the linear region 21 that is illuminated with the laser 20 and lies on the surface of the wafer 1. The axes a-b match azimuth directions in which the low-angle detection optical systems 121-3 to 121-6 detect light. Y axis (the longitudinal direction of the linear region 21 that is illuminated with the laser 20 and lies on the surface of the wafer 1, or longitudinal directions of the intermediate images 321-3 to 321-6 of the laser 20) on the surface of the wafer 1 forms angles θ3 to θ6 with the axes a-b.

As illustrated in FIGS. 7A to 7F, when the illumination optical system and the detection optical systems described in the present embodiment are used, and even if one of the detection optical systems is located in an azimuth direction that is different from a direction perpendicular to the longitudinal direction (the Y-axis direction) of the linear region 21 on the surface of the wafer 1 illuminated with the laser 20 and exists, the fields (pixels of the optical detectors) of all the detection optical systems can match each other on the surface of the wafer 1. Thus, a defect on the wafer can be detected with high detection sensitivity.

The configuration of each of the low-angle detection optical systems 121 is described above in detail. When the high-angle detection optical systems 122 that are described with reference to FIG. 2 each have the same configuration (of the low-angle detection optical systems 121) described with reference to FIG. 3, the high-angle detection optical systems 122 can image the linear region 21 on the surface of the wafer 1 illuminated with the laser 20. Specifically, the optical system 360 (illustrated in FIG. 1) of the high-angle detection optical systems 122 includes the first imaging optical system 330, the diffraction grating 340 and the second imaging optical system 333, which are described with reference to FIG. 3. The optical detector 361 (illustrated in FIG. 1) of each of the high-angle detection optical systems 122 includes the photomultiplier (described with reference to FIG. 5) that is of the multi-anode type and has the plurality of light receiving surfaces. Thus, each of the high-angle detection optical systems 122 has the same configuration as that of the low-angle detection optical systems 121.

According to the present embodiment, the linear region 21 on the surface of the wafer 1 illuminated with the laser 20 is imaged and the fields of the detection optical systems located in the plural azimuth directions and the plural elevation directions match each other. In this manner, the images of the linear region 21 can be obtained. Thus, it is possible to synthesize and process the images that are obtained by the detection optical systems and this makes it possible to detect and classy a defect in detail.

In addition, defect detecting signals detected by the low-angle detection optical systems 121 and defect detecting signals detected by the high-angle detection optical systems 122 are synthesized so as to detect a defect. This makes it possible to improve the sensitivity for detecting the defect and the accuracy of classifying the defect, compared with the method in which the detection optical systems are independently used.

In addition, as illustrated in FIG. 2, the low-angle detection optical systems 121 and the high-angle detection optical systems 122 are arranged in the plural azimuth directions and the plural elevation directions. Light reflected and scattered from the linear region 21 on the surfaced of the wafer 1 illuminated with the laser 20 is detected from the plural azimuth directions and the plural elevation directions. A detection optical system that can detect a large amount of light scattered from defects that are different in types, sizes, shapes and the like is selected from among the detection optical systems and detect the defects. Thus, it is possible to improve the sensitivity for detecting defects and the accuracy of classifying the detected defects. In addition, a noise signal component generated due to roughness of the surface of the wafer can be extracted from a signal output from a detector that detects light reflected and scattered from the defect, said detector is located in a direction in which an intensity of light reflected and scattered from a defect on the wafer 1 is weak. By processing the defect detecting signals by using the extracted noise signal component, it makes possible to detect the small defect without inhibiting the signal of the defect from being hidden by the noise signal component and improve the sensitivity for detecting the defect.

In the configuration illustrated in FIGS. 3 and 4, the analyzer 360 may rotate at an arbitrary angle around the main optical axis and be fixed, whereby only a specific polarized light component may be selectively detected. There is a case in which the ratio of a light component (signal component)

scattered from a defect (foreign material, a flaw of the surface, or the like) to a light component (noise component) scattered from the surface of the wafer 1 can be increased when the analyzer detects light. This makes it possible to improve the sensitivity for detecting the defect.

However, a polarization direction of a P-polarized light component (polarized in a direction perpendicular to the surface of the wafer 1 or parallel to the plane 300) of the light scattered from the illuminated region 21 is different by 90 degrees from a polarization direction of an S-polarized light component (to be incident on the diffraction grating 340 and detected) of the light scattered from the illuminated region 21, for example. The diffraction efficiency of the diffraction grating varies depending on the polarization of light incident on the diffraction grating. The diffraction efficiency (light use efficiency) of the diffraction grating 340 can be controlled in a constant level by adjusting a rotational direction of the half-wavelength plate 361 in accordance with a detection condition (rotational angle of the analyzer 360) of the analyzer 360 and maintaining, at a constant level, the polarization direction of the light to be incident on the diffraction grating 340.

For example, in the case illustrated in FIG. 6A, when the rotation of the half-wavelength plate is adjusted so that the light is incident on the diffraction grating 340 in a direction perpendicular to the axis a-b, the maximum diffraction efficiency can be obtained.

In the configuration of the illumination optical system 110, the optical path of the laser 20 emitted by the laser light source 4 is switched between the path for the vertical illumination and the path for the oblique illumination by the optical path changing mirror 6, as illustrated in FIG. 1. The oblique illumination optical system is advantageous in detection of a relatively small defect. The vertical illumination optical system can improve the accuracy of classifying a defect by synthesizing a detection result obtained by the vertical illumination with a detection result obtained by the oblique illumination.

Next, a method for detecting a defect on the wafer using the illumination optical system and the detection optical systems described in the present embodiment is described. In the present embodiment, at the time of defect inspection, the wafer 1 is place on the rotary table 2 and the rotary table 2 drives the stage 3 by driving the stage 3 in synchronization with the rotation of the rotary table 2. By driving the stage 3 as above, the illuminated linear region that lies on the wafer illuminated by the illumination optical system is continuously moved in one direction, that is, the longitudinal direction of the linear region. The moving length of the wafer, during one rotation, is to be set to the length equal to or shorter than a half of the length of the illuminated linear region in the longitudinal direction. Accordingly, a defect on the wafer is to pass through the illuminated linear region plural times during the inspection, and signals that are obtained by the same detection optical system can be summed and processed. It is, therefore, possible to improve the sensitivity for detecting a defect and improve the accuracy of detecting the position of the defect.

A principle of detecting signals is described with reference to FIGS. 8A and 8B. When the wafer 1 is rotated at the certain angular velocity in the direction indicated by the arrow 11, a foreign material adhering to the surface of the wafer passes through the linear region 21 in the X-axis direction (scanning). Since the wafer 1 translates (in the direction indicated by the arrow 12 or the longitudinal direction of the illuminated linear region 21) while rotating, the foreign material can be periodically detected with the setting of the constant relationship between the rotational period and the translation pitch in the Y-axis direction of the wafer 1.

Figure 8A:
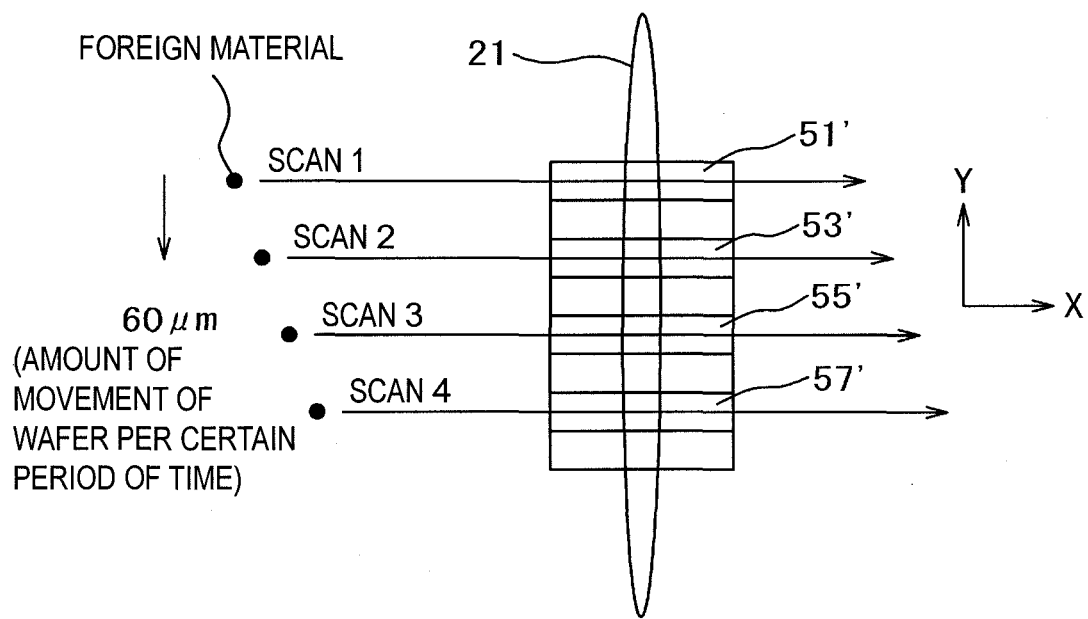
FIG. 8A is a plan view of a light receiving surface of the line sensor and illustrates the state in which the amount of a translation of the wafer per certain period of time when an image is projected on the surface of the line sensor is equal to a distance corresponding to two pixels of the line sensor, and in which images of a foreign material pass through the surface of the line sensor when scanning is performed four times.

FIG. 8A illustrates a relationship among the linear region 21 on the surface of the wafer 1 illuminated with the laser 20, the pixel array of the light receiving surfaces of the optical detector 350, and the position of a defect (foreign material) on the wafer 1. The feed rate of the wafer 1 in the longitudinal direction of the illuminated linear region 21 during one rotation of the wafer 1 is equal to a length corresponding to two pixels of the optical detector 350, and the wafer 1 is rotated four times.

Figure 8B:
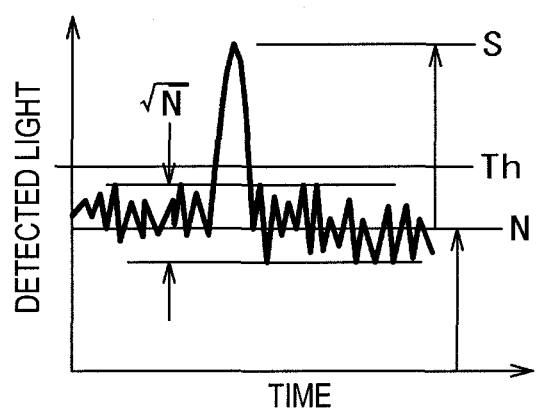
FIG. 8B is a graph illustrating results obtained by overlapping signals that are detected from a foreign material when scanning is performed four times.

FIG. 8B illustrates summed up signals which are detected during the four rotations of the wafer 1 in FIG. 8A. By shifting the signals detected during the four rotations in FIG. 8A by the length equal to the feed rate of the wafer 1 during one rotation of the wafer 1 and corresponding to two pixels of the optical detector 350 and summing the signals, the signals can be obtained as signals detected from the same location on the wafer 1. Thus, signal-to-noise ratios of signals detected from a defect can be improved by detecting the signals from the same location, summing the signals, cancelling randomly generated noise signals and highlighting the signals of the defect. Therefore, the defect can be detected using a relatively low threshold Th, and the sensitivity for detecting the defect can be improved.

As described above, the signals that are detected by the detection optical systems are subjected to pattern matching using Haze signals so that the amount of pixel shift and a direction the pixel is shifted are detected. The coordinates of the detected signals are corrected based on the amount of pixel shift and the direction the pixel is shifted. Thus, signals of light scattered from substantially the same region can be summed with high accuracy.

In addition, a variation in the height of the wafer and a direction in which the height of the wafer varies are detected by monitoring positional shift of the illuminated region or monitoring specularly-reflected light of the laser beam with which the wafer is illuminated. The coordinates of the detected signals are corrected based on a monitored signal. Thus, signals of light scattered from substantially the same region can be summed with high accuracy.

The line sensors are rotated around the optical axes and arranged corresponding to the azimuths θ1 to θ6 at which the detection optical systems are arranged, and optical magnifications of the detection optical systems are adjusted in accordance with the azimuths θ1 to θ6 so that it makes possible to avoid a pixel from being shifted due to a variation in the height of the wafer.

Figure 9:
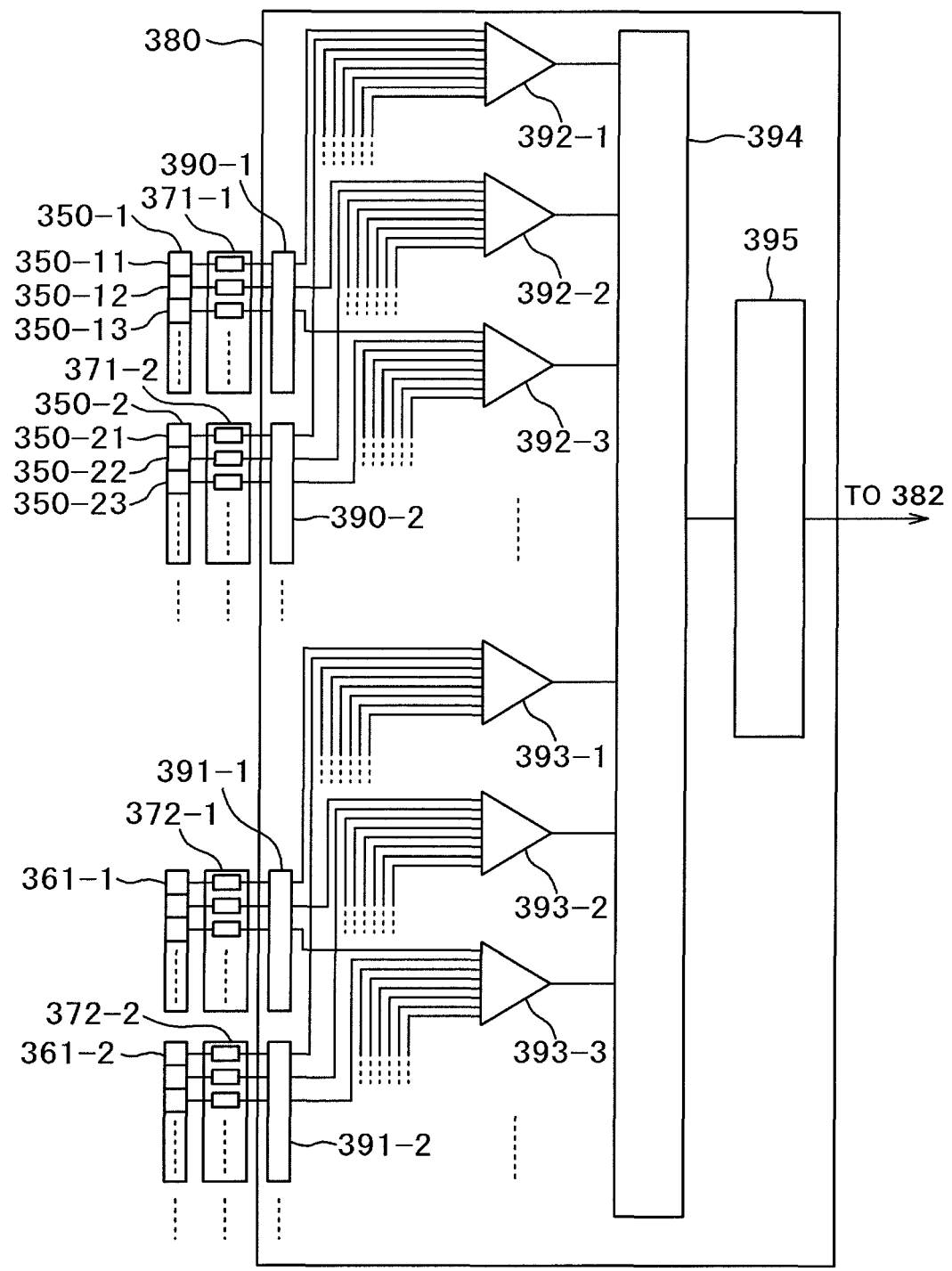
FIG. 9 is a block diagram illustrating an outline configuration of a signal processing unit that processes signals output from photomultipliers according to the first embodiment.

The signal processing circuit 381 is described with reference to FIG. 9. The signal processing circuit 381 processes signals output from the plurality of light receiving surfaces of each of the optical detectors 350 that have detected optical images acquired by the low-angle detection optical systems 121. Specifically, analog signals output from eight light receiving surfaces 350-11 to 350-18 of the optical detector 350-1 corresponding to the unit 121-1 (illustrated in FIG. 2) that is the low-angle detection optical system 121 are converted into digital signals by an A/D converter 371-1. After that, the digital signals are input to the signal processing unit 380. A switching unit 390-1 turns on and off the signals. When the switching unit 390-1 is turned on, the signal that is obtained from the light receiving surface 350-11 is input to an adder 392-1. The digital signals are added to signals output from corresponding light receiving surfaces of the other optical detectors such as a signal output from a light receiving surface 350-21 of the optical detector 350-2 corresponding to the unit 121-2 (that is the low-angle detection optical system 121) and a signal output from a light receiving surface 350-31 of the optical detector 350-3 corresponding to the unit 121-3 (that is the low-angle detection optical system 121).

The analog signal output from the light receiving surface 350-12 of the optical detector 350-1 is converted into the digital signal by an A/D converter 371-1. After that, the signal is input to the signal processing unit 380. The switching unit 390-1 turns on and off the signal. When the switching unit 390-1 is turned on, the signal is input to an adder 392-2. The digital signals are added to signals output from corresponding light receiving surfaces of the other optical detectors such as a signal output from a light receiving surface 350-22 of the optical detector 350-2 corresponding to the unit 121-2 (that is the low-angle detection optical system 121) and a signal output from a light receiving surface 350-32 of the optical detector 350-3 corresponding to the unit 121-3 (that is the low-angle detection optical system 121). In addition, the signal that is output from the light receiving surface 350-13 of the optical detector 350-1 is converted into the digital signal by the A/D converter 371-1. After that, the signal is input to the signal processing unit 380, passes through the switching unit 390-1, and then the signal is input to an adder 392-3. The digital signals are added to signals output from corresponding light receiving surfaces of the other optical detectors such as a signal output from a light receiving surface 350-23 of the optical detector 350-2 and a signal output from a light receiving surface 350-33 of the optical detector 350-3 corresponding to the unit 121-3.

In this manner, signals that are output from corresponding light receiving surfaces of the optical detectors 350-1 to 350-6 are summed by adders 392-1 to 392-6. In this case, the switching units 390-1 to 390-6 each turn on and off the signals output from the optical detectors 350-1 to 350-6, and thereby signals are selected from among the signals output from the optical detectors 350-1 to 350-6 and the selected signals are summed. For example, of the detectors illustrated in FIG. 2, when an intense noise component is contained in forward-scattered light by the illumination with the laser 20, the output signals from the optical detectors 350-3 and 350-4 that detect the forward-scattered light, correspond to the units 121-3 and 121-4 (that are the low-angle detection optical systems 121) may be turned off, and the signals output from the other optical detectors may be summed by the adders 392-1 to 392-6.

Signals that are obtained by summing the signals by means of the adders 392-1 to 392-6 are input to a signal synthesizing unit 394. Then, the signal synthesizing unit 394 synthesizes the signals to form a synthesized signal. The signal synthesizing unit 394 transmits the synthesized signal to a signal processing circuit unit 395, then, the signal processing circuit unit 395 processes the synthesized signal and extracts information of the type, size and position of a defect. The signal processing circuit unit 395 transmits information extracted by the signal processing circuit unit 395 to a display unit 82. Then, the display unit 82 displays the information on the detected defect on a screen. In addition, the signal processing circuit unit 395 transmits information extracted by the signal processing circuit unit 395 to the controller 382. The controller 382 associates the information with other information such as a lot number of the wafer, information on a date and time of the inspection, information on the inspection device, and information on conditions for the inspection and then the information are stored in storage means 384.

Figure 10:
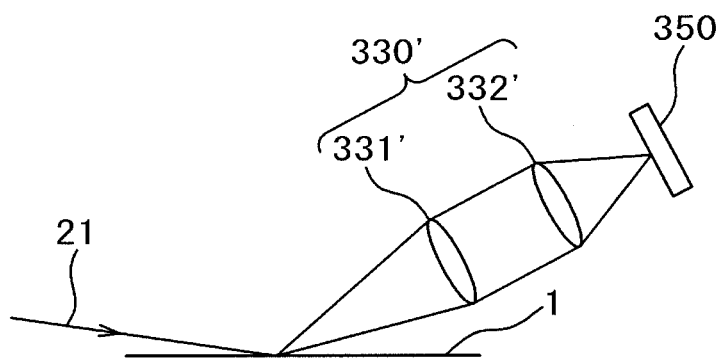
FIG. 10 is a side cross-sectional view of an outline configuration of a modified example of a low-angle detection optical system that is arranged in a direction perpendicular to a direction of extension of the illuminated linear region on the wafer, the low-angle detection optical system includes a focusing lens and an imaging lens.

According to the first embodiment, the example in which the imaging optical systems employing the diffraction gratings 340 are used in the detection optical systems arranged at all the azimuths as illustrated in FIGS. 7A to 7F. The detection optical systems that are the units 121-2 and 121-5 illustrated in FIG. 2 may each use an imaging optical system 330' that includes a general collecting lens 331' and a general imaging lens 332' without using the diffraction grating 340, as illustrated in FIG. 10.

Second Embodiment

A surface inspection device according to a second embodiment of the present invention is described below.

The configuration of the surface inspection device according to the second embodiment is basically the same as the configuration illustrated in FIG. 1. However, the configuration of a collecting optical system 360 of each of the high-angle detection optical systems 122 according to the second embodiment is different from the first embodiment.

In the first embodiment, the optical system illustrated in FIG. 4 is employed as each of the low-angle detection optical systems 121 and the high-angle detection optical systems 122. When the linear region is illuminated from the oblique direction, a large amount of light is reflected and scattered from a minute foreign material at a low evaluation and only a small amount of light is scattered from the minute foreign material at a high evaluation in some cases.

Hence, for detection of a minute defect, even if the high-angle detection optical systems 122 are configured to detect the defect with a high sensitivity of the same level as the sensitivity of each of the low-angle detection optical systems 121, there is not much of an advantage.

In the present embodiment, the high-angle detection optical systems 122 each include a simple collecting optical system and have a relatively simpler configuration than the high-angle detection optical systems 122 according to the first embodiment.

Figure 11:
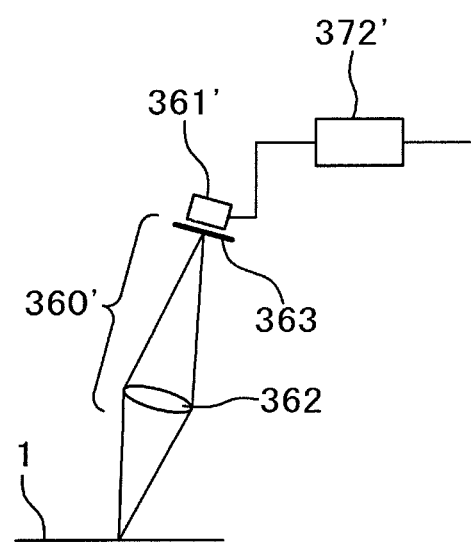
FIG. 11 is a side cross-sectional view of a high-angle detection optical system according to a second embodiment, while the high-angle detection optical system includes a photomultiplier of a single anode type, a slit plate and a collecting lens.

In the first embodiment, the configuration of the collecting optical system 360 of each of the high-angle detection optical systems 122 is basically the same as the configuration of the collecting optical system 360 (illustrated in FIG. 4) of each of the low-angle detection optical systems 121. In the present embodiment, the diffraction grating 340 is not used, and the collecting optical system is employed instead of the first imaging optical system 330 and the second imaging optical system 333. FIG. 11 illustrates the configuration of the optical system in the second embodiment. Specifically, in the second embodiment, the high-angle detection optical systems each include a collecting optical system 360' instead of the imaging optical systems 360 used in the first embodiment, while the collecting optical system 360' includes a collecting lens 362 and a pinhole 363, as illustrated in FIG. 11. In the second embodiment, the high-angle detection optical systems each include a photomultiplier 361' of a single anode type instead of the photomultiplier 361 that is of the multi-anode type and has the plurality of light receiving surfaces. The fields of the high-angle detection optical systems in the second embodiment are each reduced to an area corresponding to a part of the linear region 21 (illuminated with the laser 20 and laying on the surface of the wafer 1) by the pinholes 363 arranged in front of the photomultipliers 361' so that noise is reduced and scattered light is detected by the high-angle detection optical systems.

Figure 12:
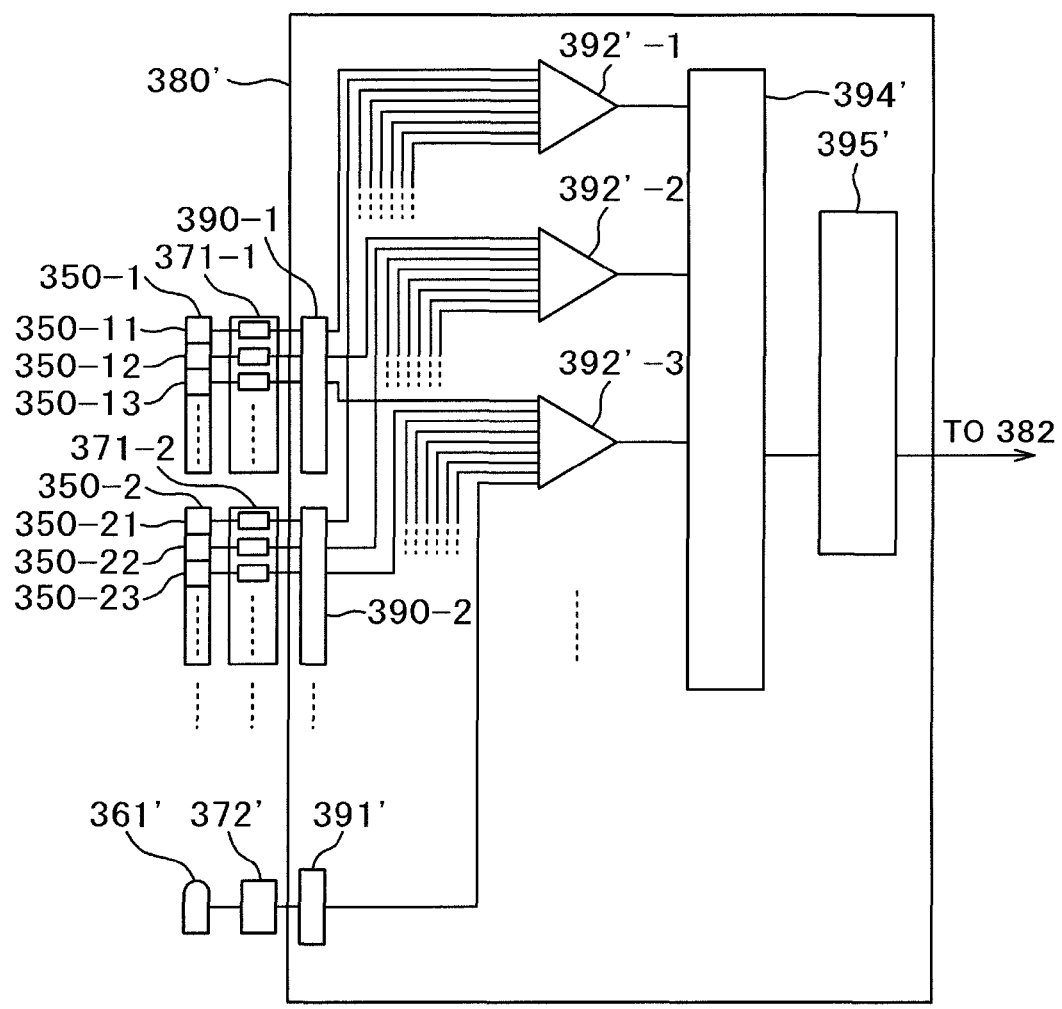
FIG. 12 is a block diagram illustrating an outline configuration of a signal processing unit that processes signals output from the photomultipliers according to the second embodiment.

In the present embodiment, the low-angle detection optical systems 121 each use the photomultiplier 350 (that is of the multi-anode type and has the plurality of light receiving surfaces) to detect an optical image, while the high-angle detection optical systems 122 each use the photomultiplier 361' of the single anode type. Output signals from the detectors of the detection optical systems are processed by a signal processing unit 380' configured as illustrated in FIG. 12.

Specifically, signals of scattered light detected by the light receiving surfaces 350-11 to 350-18, 350-21 to 350-28, and 350-61 to 350-68 of the photomultipliers 350-1 to 350-6 included in the units 121-1 to 121-6 that are the low-angle detection optical systems 121 arranged as illustrated in FIG. 2 are converted into digital signals by the A/D converters 371-1 to 371-6. Analog signals that are output from the photomultipliers 361' included in the high-angle detection optical systems 122 are converted into digital signals by A/D converters 372'. The digital signals obtained by the conversion performed by the A/D converters 372' and output from the photomultipliers 361' are added by an adder 392-3' to signals (signals output from the light receiving surfaces 350-13, 350-23, and 350-63 in the case of FIG. 11) output from the light receiving surfaces that have detected light that is among scattered light detected by the light receiving surfaces 350-11 to 350-18, 350-21 to 350-28, . . . , and 350-61 to 350-68 of the photomultipliers 350-1 to 350-6 of the low-angle detection optical systems 121 and has been scattered from parts located near fields of the pinholes 363. An adder 392'-1 sums signals output from the receiving light surfaces 350-11, 350-21, . . . , and 350-61 of the photomultipliers 350-1 to 350-6 of the low-angle detection optical systems 121. An adder 392'-2 sums signals output from the receiving light surfaces 350-12, 350-22, . . . , and 350-62 of the photomultipliers 350-1 to 350-6 of the low-angle detection optical systems 121. An adder 392'-4 (not shown) sums signals output from the receiving light surfaces 350-14, 350-24, . . . , and 350-64 of the photomultipliers 350-1 to 350-6 of the low-angle detection optical systems 121. An adder 392'-5 (not shown) sums signals output from the receiving light surfaces 350-15, 350-25, . . . , and 350-65 of the photomultipliers 350-1 to 350-6 of the low-angle detection optical systems 121. An adder 392'-6 (not shown) sums signals output from the receiving light surfaces 350-16, 350-26, . . . , and 350-66 of the photomultipliers 350-1 to 350-6 of the low-angle detection optical systems 121.

The switching units 390-1 to 390-6 and 391' turn on and off the signals output from the optical detectors 350-1 to 350-6 and 361' so as to select signals from among the signals output from the optical detectors 350-1 to 350-6 and 361' and sum the selected signals. For example, when an intense noise component is contained in forward-scattered light by the illumination with the laser 20, the signals output from the optical detectors 350-3 and 350-4 that detect the forward-scattered light, correspond to the units 121-3 and 121-4 (that are the low-angle detection optical systems 121) and are among the detectors illustrated in FIG. 2 may be turned off, and the signals output from the other optical detectors may be summed by the adders 392-1 to 392-6.

Signals that are obtained by summing the signals by means of the adders 392'-1 to 392'-6 are input to a signal synthesizing unit 394'. Then, the signal synthesizing unit 394' synthesizes the signals to form a synthesized signal. The signal synthesizing unit 394' transmits the synthesized signal to a signal processing circuit unit 395', then, the signal processing circuit unit 395' processes the synthesized signal and extracts information of the type, size and position of a defect. The signal processing circuit unit 395' transmits information extracted by the signal processing circuit unit 395' to a display unit 82. Then, the display unit 82 displays the information on the detected defect on a screen. In addition, the signal processing circuit unit 395' transmits information extracted by the signal processing circuit unit 395' to the controller 382. The controller 382 associates the information with other information such as a lot number of the wafer, information on a date and time of the inspection, information on the inspection device, and information on conditions for the inspection and then the information are stored in storage means 384.

According to the present embodiment, the linear region 21 on the surface of the wafer 1 illuminated with the laser 20 is imaged and the fields of the detection optical systems located in the plural azimuth directions and the plural elevation directions match each other. In this manner, the images of the linear region 21 can be obtained. Thus, it is possible to synthesize and process the images that are obtained by the detection optical systems and this makes it possible to detect and classy a defect in detail.

In addition, defect detecting signals detected by the low-angle detection optical systems 121 and defect detecting signals detected by the high-angle detection optical systems 122 are synthesized so as to detect a defect. This makes it possible to improve the sensitivity for detecting the defect and the accuracy of classifying the defect, compared with the method in which the detection optical systems are independently used.

In addition, as illustrated in FIG. 2, the low-angle detection optical systems 121 and the high-angle detection optical systems 122 are arranged in the plural azimuth directions and the plural elevation directions. Light reflected and scattered from the linear region 21 on the surface of the wafer 1 illuminated with the laser 20 is detected from the plural azimuth directions and the plural elevation directions. A detection optical system that can detect a large amount of light scattered from defects that are different in types, sizes, shapes and the like is selected from among the detection optical systems and detect the defects. Thus, it is possible to improve the sensitivity for detecting defects and the accuracy of classifying the detected defects. In addition, a noise signal component generated due to roughness of the surface of the wafer can be extracted from a signal output from a detector that detects light reflected and scattered from the defect, said detector is located in a direction in which an intensity of light reflected and scattered from a defect on the wafer is weak. By processing the defect detecting signals by using the extracted noise signal component, it makes possible to detect the small defect without inhibiting the signal of the defect from being hidden by the noise signal component and improve the sensitivity for detecting the defect.

In the configuration of the illumination optical system 110, the optical path of the laser 20 emitted by the laser light source 4 is switched between the path for the vertical illumination and the path for the oblique illumination by the optical path changing mirror 6, as illustrated in FIG. 1. The oblique illumination optical system is advantageous in detection of a relatively small defect. The vertical illumination optical system can improve the accuracy of classifying a defect by synthesizing a detection result obtained by the vertical illumination with a detection result obtained by the oblique illumination.

In addition, since the high-angle detection optical systems each include the photomultiplier 361' of the single anode type, the configurations of the high-angle detection optical systems according to the second embodiment are relatively simpler than the configurations of the high-angle detection optical systems according to the first embodiment. Thus, even when the high-angle detection optical systems are manufactured at relative low cost, the high-angle detection optical systems can each detect a small defect and have an improved sensitivity for detecting a defect.

In the same manner as described in the last part of the first embodiment, the detection optical systems that are the units 121-2 and 121-5 illustrated in FIG. 2 may each use an imaging optical system 330' that includes a general collecting lens 331' and a general imaging lens 332' without using the diffraction grating 340, as illustrated in FIG. 10 in the second embodiment.

The first and the second embodiments describe the method for detecting a defect while causing the rotary table 2 to rotate the wafer. However, the present invention is not limited to this method. Instead of the combination of the rotary table 2 and the stage 3, a stage that is capable of moving in the X-axis direction and a stage that is capable of moving in the Y-axis direction may be synthesized and used. In this case, while the stages continuously move in a direction perpendicular to the longitudinal direction of the linear region 21 on the surface of the wafer 1, the high-angle detection optical systems and the low-angle detection optical systems image the linear region 21 and detect a defect on the wafer.

INDUSTRIAL APPLICABILITY

In order to maintain or improve the manufacturing yield of products manufactured in a manufacturing line for semiconductor devices, a dummy wafer is used so that a foreign material attached to the substrate (wafer) in a manufacturing process, a flaw occurring on the surface of the wafer, defective crystal and the like are inspected. The present invention is applicable to the inspection.

REFERENCE SIGNS LIST

1 ... Wafer, 2 ... Rotary table, 3 ... Stage, 4 ... Laser light source, 100 ... Stage unit, 110 ... Illumination optical system, 120 ... Detection optical system, 121 ... Low-angle detection optical system, 122 ... High-angle detection optical system, 130 ... Processing control unit, 330 ... First imaging optical system, 333 ... Second imaging optical system, 340 ... Diffraction grating, 350, 361 ... Photomultiplier, 360 ... Optical system, 361' ... Photomultiplier, 362 ... Collecting lens, 363 ... Pinhole, 380, 380' ... Signal processing unit 380 ... Output unit, 382 ... Whole controller, 383 ... Stage controller, 384 ... Storage unit

The invention claimed is:

1. A device for inspecting a defect, comprising:
    table means for holding a sample;
    illumination means for illuminating a linear region that lies on the sample held by the table means;
    high-angle detection optical system means having a plurality of optical image detectors, the optical image detectors detecting, from plural azimuth directions, light scattered from the linear region that lies on the sample illuminated by the illumination means, the scattered light being scattered from the linear region at a high evaluation;
    low-angle detection optical system means having plural optical image detectors, the optical image detectors detecting, from plural azimuth directions, light scattered from the linear region that lies on the sample illuminated by the illumination means, the scattered light scattered from the linear region at a low evaluation; and
    a signal processing unit that processes a signal obtained by detecting the light scattered from the sample by means of the high-angle detection optical system means and a signal obtained by detecting the light scattered from the sample by means of the low-angle detection optical system means to detect a defect on the sample,
    wherein the optical image detector of the low-angle detection optical system is formed by synthesizing a first imaging lens group, a diffraction grating, a second imaging lens group and an image detector having plural light receiving surfaces, and
    wherein the signal processing unit sums and processes signals detected by light receiving surfaces that are included in the plural optical image detectors of the low-angle detection optical system means and correspond to each other.

2. The defect inspection device according to claim 1, wherein the table means for holding the sample includes a rotary table for rotating the sample and a stage for moving the sample in a certain direction.

3. The defect inspection device according to claim 1, wherein the high-angle detection optical system has photomultipliers that are located in the plural azimuth directions with respect to the linear region that lies on the sample illuminated by the illumination means, and collect and detect the light scattered from the linear region that lies on the sample.

* * * * *